US011808913B2

(12) United States Patent
Mangeat et al.

(10) Patent No.: US 11,808,913 B2
(45) Date of Patent: Nov. 7, 2023

(54) OPTICAL PROBE AND METHOD FOR IN SITU SOIL ANALYSIS

(71) Applicant: 9371-0184 QUÉBEC INC., Montreal (CA)

(72) Inventors: Gabriel Mangeat, Montreal (CA); Benjamin De Leener, Montreal (CA)

(73) Assignee: 9371-0184 QUÉBEC INC., Montreal (CA)

( * ) Notice: Subject to any disclaimer, the term of this patent is extended or adjusted under 35 U.S.C. 154(b) by 0 days.

(21) Appl. No.: 17/277,148

(22) PCT Filed: Sep. 18, 2019

(86) PCT No.: PCT/CA2019/051322
§ 371 (c)(1),
(2) Date: Mar. 17, 2021

(87) PCT Pub. No.: WO2020/056506
PCT Pub. Date: Mar. 26, 2020

(65) Prior Publication Data
US 2021/0356622 A1 Nov. 18, 2021

Related U.S. Application Data

(60) Provisional application No. 62/732,755, filed on Sep. 18, 2018.

(51) Int. Cl.
*G01V 8/02* (2006.01)
*G01N 21/85* (2006.01)
*G01N 21/31* (2006.01)

(52) U.S. Cl.
CPC ........... *G01V 8/02* (2013.01); *G01N 21/8507* (2013.01); *G01N 2021/3181* (2013.01)

(58) Field of Classification Search
CPC .... E21B 49/00; G01N 21/8507; G01N 21/64; G01N 2021/3181; G01N 33/24; G01N 2021/855; G01J 3/0205; G01J 3/0291
See application file for complete search history.

(56) References Cited

U.S. PATENT DOCUMENTS 4,994,671 A 2/1991 Safinya et al.
5,128,882 A * 7/1992 Cooper .................... G01V 8/02
356/73

(Continued)

FOREIGN PATENT DOCUMENTS

CN 104483285 A * 4/2015
DE 112015002036 T5 * 7/2017

(Continued)

OTHER PUBLICATIONS

PCT "International Search Report" for PCT/CA2019/051322 dated Dec. 12, 2019, 4 pages.

(Continued)

*Primary Examiner* — Tarifur R Chowdhury
*Assistant Examiner* — Roberto Fabian, Jr.
(74) *Attorney, Agent, or Firm* — Amundsen Davis. LLC

(57) ABSTRACT

An optical probe and method for analysing a soil located in an underground area are provided. The optical probe includes a probe head insertable into the underground area, the probe head including a transparent wall defining a hollow chamber within the probe head; a light source mounted in the hollow chamber, configured to generate an illumination beam towards the soil, the illumination beam passing through the transparent wall to irradiate the soil, thereby producing a resulting light emanating from the soil, a portion of the resulting light returning towards the probe head and being guided in the transparent wall by total internal reflection along the optical path; a detector configured to receive the portion of the resulting light and output- (Continued)

ting an output signal representative of characteristic(s) of the soil; and an optical element guiding the portion of the resulting light from the transparent wall to the detector.

21 Claims, 14 Drawing Sheets

(56) References Cited

U.S. PATENT DOCUMENTS

| | | | |
|---|---|---|---|
| 5,548,115 A * | 8/1996 | Ballard | G01N 33/241 250/301 |
| 5,739,536 A * | 4/1998 | Bucholtz | G01J 3/0291 250/341.2 |
| 6,393,927 B1 | 5/2002 | Biggs et al. | |
| 8,325,336 B2 | 12/2012 | Preiner et al. | |
| 8,444,937 B2 | 5/2013 | Tuli et al. | |
| 10,337,283 B2 | 7/2019 | Gottumukkala et al. | |
| 10,345,283 B1 | 7/2019 | Laird et al. | |
| 10,458,907 B2 | 10/2019 | Roodenko | |
| 2002/0039186 A1* | 4/2002 | Rosenberg | G01N 21/8507 356/432 |
| 2010/0148785 A1* | 6/2010 | Schaefer | G01V 8/02 324/338 |
| 2010/0309463 A1 | 12/2010 | Lucke et al. | |
| 2017/0370064 A1* | 12/2017 | Morgan | G01J 3/108 |

FOREIGN PATENT DOCUMENTS

| | | |
|---|---|---|
| EP | 1484600 A2 * | 12/2004 |
| EP | 1 264 170 B1 | 2/2009 |
| EP | 3 395 147 A1 | 10/2018 |
| WO | WO-2017187088 A1 * | 11/2017 |
| WO | WO-2018112116 A1 * | 6/2018 |

OTHER PUBLICATIONS

PCT "Written Opinion" for PCT/CA2019/051322 dated Dec. 12, 2019, 5 pages.
PCT "International Preliminary Report on Patentability" for PCT/CA2019/051322 dated Mar. 23, 2021, 6 pages.
Extended European Search Report of EP 19861506.4, dated May 4, 2022, 7 pages filed herewith.

* cited by examiner

OPTICAL PROBE AND METHOD FOR IN SITU SOIL ANALYSIS

TECHNICAL FIELD

The technical field generally relates to device and method for soil analysis, and more particularly concerns an optical probe for in situ spectral analysis of a soil, as well as a method for doing the same.

BACKGROUND

Soil tests are generally performed in a laboratory. From a practical point of view, several soil samples are typically extracted from a field under investigation, before being sent to the laboratory for subsequent analyses and characterization.

However, the different characteristics of the soil samples are known to change over time, which may occur during their transport or when they are stored. Thus, the results of the analyses performed on such altered soil samples may not be representative of the soil characteristics. The characteristics of the soil also vary over space, within the same field. As laboratory characterizations are time consuming and also generally expensive, only one laboratory analysis is traditionally performed per field, resulting in a relatively poor characterization of the field.

There is thus a need for a system, device, as well as methods that address or alleviate at least some of the challenges presented above.

SUMMARY

In accordance with one aspect, there is provided an optical probe for analysing a soil located in an underground area, the optical probe including a probe head insertable into the underground area to contact the soil, the probe head including a transparent wall defining a hollow chamber within the probe head, the transparent wall having a top extremity and a bottom extremity defining an optical path therebetween; a light source mounted in the hollow chamber, the light source being configured to generate an illumination beam towards the soil, the illumination beam passing through the transparent wall to irradiate the soil, thereby producing a resulting light emanating from the soil, a portion of the resulting light returning towards the probe head and being guided in the transparent wall by total internal reflection along the optical path; a detector configured to receive the portion of the resulting light guided in the transparent wall and outputting an output signal representative of at least one characteristic of the soil; and an optical element mounted in the hollow chamber, near or at the top extremity of the transparent wall, the optical element guiding the portion of the resulting light guided in the transparent wall from the transparent wall to the detector.

In some embodiments, the light source includes a light-emitting diode configured to emit the illumination beam, the illumination beam having a spectral profile including a waveband ranging from about 350 nm to about 900 nm.

In some embodiments, the spectral profile includes a visible waveband ranging from about 400 nm to about 750 nm.

In some embodiments, the optical probe further includes a first radial lens optically coupled to the light-emitting diode for generating a collimated illuminating beam.

In some embodiments, the first radial lens is positioned at or near the bottom extremity, in the hollow chamber.

In some embodiments, the light source includes a stack of light-emitting diodes.

In some embodiments, the stack of light-emitting diodes including a white broad band light-emitting diode.

In some embodiments, the stack of light-emitting diodes includes an infrared broad band light-emitting diode.

In some embodiments, the stack of light-emitting diodes includes a blue-light emitting diode.

In some embodiments, the stack of light-emitting diodes includes an ultra-violet light-emitting diode.

In some embodiments, the stack of light-emitting diodes includes an ultra-violet light-emitting diode emitting an ultra-violet sub-beam having a spectral profile including a waveband centered around 385 nm; a blue light-emitting diode mounted on the ultra-violet light emitting diode and emitting a blue sub-beam having a spectral profile including a waveband centered around 488 nm; an infrared broad band light-emitting diode mounted on the blue-light emitting diode and emitting an infrared sub-beam having a spectral profile including a waveband ranging from about 650 nm to about 900 nm; and a white broad band light-emitting diode mounted on the infrared broad band light-emitting diode and emitting a white sub-beam having a spectral profile including a waveband ranging from about 420 nm to about 700 nm.

In some embodiments, each light-emitting diode from the stack of light-emitting diodes is optically coupled with a respective radial lens.

In some embodiments, the portion of the resulting light guided by the transparent wall includes light scattered by the soil.

In some embodiments, the portion of the resulting light guided by the transparent wall includes light reflected by the soil.

In some embodiments, the transparent is tubular and the light source is configured to irradiate the soil through 360 degrees around the probe head.

In some embodiments, the transparent wall is made from a material impermeable to a soil solution present in the soil.

In some embodiments, the transparent wall is made of clear fused quartz.

In some embodiments, the transparent wall is made of sapphire.

In some embodiments, the optical element includes an optical diffuser positioned near or at the top extremity, in the hollow chamber, the optical diffuser being optically coupled with the transparent wall for scattering the portion of the resulting light guided in the transparent wall inside the probe head.

In some embodiments, the optical probe further includes a second radial lens for focusing the light scattered by the optical diffuser towards the detector, the second radial lens being optically coupled with the optical diffuser.

In some embodiments, the second radial lens is mounted in the hollow chamber.

In some embodiments, the optical probe further includes an optical fiber located near or at the top extremity, the optical fiber guiding the portion of the resulting light guided in the transparent wall towards the detector.

In some embodiments, the optical fiber is in mechanical contact with the transparent wall.

In some embodiments, the detector is a spectrometer.

In some embodiments, the hollow chamber encloses the detector.

In some embodiments, the optical probe further includes a processor, the processor being configured to receive the output signal representative of said at least one characteristic of the soil; and determine a spectral content of the portion of the resulting light guided by the transparent wall In some embodiments, the optical probe further includes a control unit operatively connected to at least one of the light source and the detector, the control unit being configured for operating and controlling said at least one of the light source and the detector.

In some embodiments, said at least one characteristic of the soil are selected from the group consisting of: level of nutrients, level of available nutrients, ionic concentration of the soil solution, temperature, moisture, pH, level of organic matter and soil texture.

In some embodiments, the optical probe further includes a power unit including at least one battery.

In some embodiments, the at least one battery has an autonomy of about 1500 measurements.

In some embodiments, the optical probe further includes a sensing tip mounted at an extremity of the probe head, the sensing tip being configured to measure at least one of the electroconductivity and the pH of the soil.

In some embodiments, the optical probe further includes a body having a bottom end portion, the probe head being mounted to the bottom end portion.

In some embodiments, the body has a height ranging from about 30 cm to about 100 cm and the probe head has a height ranging from about 0.5 cm to about 5 cm.

In some embodiments, the probe head has an outer surface area ranging from about 400 mm$^2$ to about 4000 mm$^2$.

In accordance with another aspect, there is provided a method for analysing a soil located in an underground area, the method including steps of inserting a probe head in the underground area to contact the soil, the probe head including a transparent wall defining a hollow chamber within the probe head, the transparent wall having a top extremity and a bottom extremity defining an optical path therebetween; projecting an illuminating beam towards the soil and through the transparent wall to irradiate the soil, thereby producing a resulting light emanating from the soil and returning towards the probe head; guiding, in the transparent wall, a portion of the resulting light by total internal reflection along the optical path; guiding, with an optical element, the portion of the resulting light guided in the transparent wall with an optical element from the transparent wall to a detector; detecting the portion of the resulting light guided in the transparent wall; and outputting an output signal representative of the at least one characteristic of the soil.

In some embodiments, the method further includes processing the output signal representative of said at least one characteristic of the soil.

In some embodiments, said processing the output signal representative of said at least one characteristic of the soil includes: receiving the output signal representative of said at least one characteristic of the soil; and determining a spectral content of the portion of the resulting light guided in the transparent wall.

In some embodiments, said at least one characteristic of the soil are selected from the group consisting of: level of nutrients, level of available nutrients, ionic concentration of the soil solution, temperature, moisture, pH, level of organic matter and soil texture.

In some embodiments, the method further includes measuring at least one of the electroconductivity and the pH of the soil with a sensing tip mounted at an extremity of the probe head.

In some embodiments, the method further includes wirelessly operating and controlling at least one of the light source and the detector.

In some embodiments, further includes drilling a hole in the underground area to receive the probe head therein.

In some embodiments, said inserting the probe head in the underground area to contact the soil includes pushing the probe head towards the underground area.

In some embodiments, the method further includes rotating the probe head as the probe head is pushed towards the underground area.

In some embodiments, said inserting the probe head in the underground area to contact the soil includes inserting the probe head in a pre-made or pre-drilled hole.

In some embodiments, said inserting the probe head in the underground area to contact the soil includes inserting the probe head at a depth ranging from about 0 cm to about 80 cm under the soil surface.

In some embodiments, the method further includes obtaining one or more subsequent output signals representative of at least one characteristic of the soil, each subsequent output signal being measured at a different location of a field or at a different depth of the field.

In some embodiments, said projecting an illuminating beam towards the soil and through the transparent wall to irradiate the soil includes irradiating the soil through 360 degrees around the probe head.

In accordance with one implementation, there is provided an optical probe for analysing a soil located in an underground area using an illuminating beam. The optical probe includes a light source for generating the illuminating beam, a probe head insertable into the underground area to contact the soil, the probe head comprising a light collector for collecting and trapping a resulting light emanating from the soil after irradiation of the soil by the illuminating beam, and a detector for receiving the resulting light collected and trapped by the light collector and producing an output signal representative of at least one characteristic of the soil.

In accordance with another implementation, there is provided a method for analysing a soil located in an underground area using an illuminating beam. The method includes steps of inserting an optical probe including a light collector in the underground area to contact the soil; projecting the illuminating beam towards the soil through the light collector; collecting a resulting light emanating from the soil with the light collector; detecting the resulting light reflected by the soil; and outputting a signal representative of the soil condition.

In some embodiments, the light source includes at least one light-emitting diode.

In some embodiments, the spectral profile comprises a waveband ranging from about 350 nm to about 900 nm.

In some embodiments, the spectral profile comprises a visible waveband ranging from about 400 nm to about 750 nm.

In some embodiments, the light collector is optically transparent to the spectral profile of the illuminating beam.

In some embodiments, the light collector guides the resulting light scattered by the soil with total internal reflection.

In some embodiments, the light collector guides the resulting light reflected by the soil with total internal reflection.

In some embodiments, the light collector is a tubular-shaped light collector having an inner surface and an outer surface.

In some embodiments, the optical probe further includes a first radial lens optically coupled to the light source for generating a collimated illuminating beam towards the outer cylindrical periphery.

In some embodiments, the first radial lens is concentrically mounted within the light collector In some embodiments, the collimated illuminating beam is generated in a radial direction of the tubular-shaped light collector.

In some embodiments, the light collector is made of clear fused quartz.

In some embodiments, the light collector is made of sapphire.

In some embodiments, the probe head has an inner portion defined by an inner periphery, and the optical probe further includes an optical diffuser optically coupled with the light collector for scattering the resulting light reflected by the light collector towards the inner portion of the probe head and a second radial lens for focusing the scattered light towards the detector.

In some embodiments, the second radial lens is concentrically mounted within the light collector In some embodiments, the optical diffuser conforms with the inner periphery of the inner portion of the probe head.

In some embodiments, the optical probe further includes an optical fiber for guiding the light reflected from the light collector towards the detector.

In some embodiments, the light collector comprises a hole for receiving the optical fiber therein.

In some embodiments, the detector is a spectrometer.

In some embodiments, the light collector encloses at least one of the light source and the detector.

In some embodiments, the optical probe further includes a processor for processing the signal representative of said at least one characteristic of the soil.

In some embodiment, the optical probe further includes a control unit for operating and controlling at least one of the light source and the detector, the control unit being operatively connectable to the processor.

In some embodiments, the optical probe further includes a power unit including at least one battery.

In some embodiments, the at least one battery has a cycle life of about 1500 measurements.

In some embodiments, the body has a height ranging from about 30 cm to about 100 cm.

In some embodiments, the probe head has a height of about 5 cm.

In some embodiments, the probe head has an outer surface ranging from about 400 mm$^2$ to about 4000 mm$^2$.

In some embodiments, the characteristics of the soils are selected from the group consisting of: level of nutrients, level of available nutrients (or ionic concentration of the soil solution), temperature, moisture, pH, level of organic matter, and texture.

In some embodiments, the optical probe further includes a sensing tip mounted at an extremity of the probe head, the sensing tip being configured to measure at least one of the electroconductivity and the pH of the soil.

Other features and advantages of the present description will become more apparent upon reading of the following non-restrictive description of specific embodiments thereof, given by way of example only with reference to the accompanying drawings.

DETAILED DESCRIPTION

Figure 1:
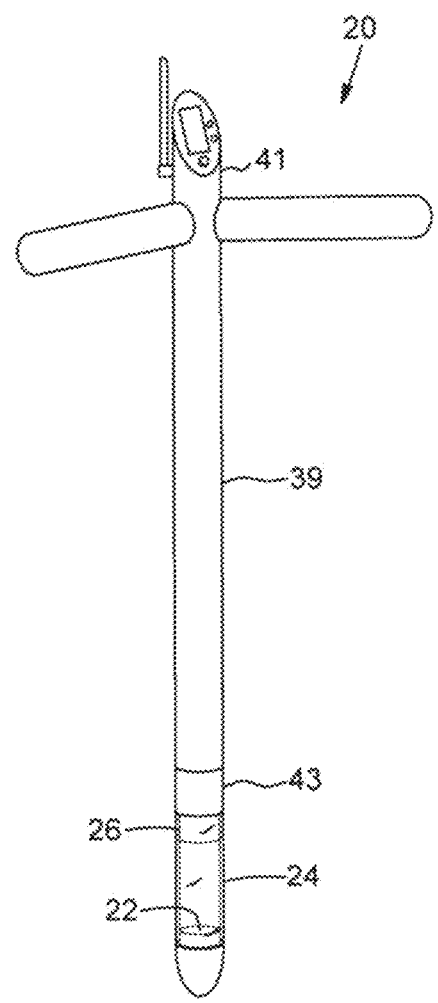
FIG. 1 is a side view of an optical probe for soil spectral analysis, in accordance with one embodiment.

In the following description, similar features in the drawings have been given similar reference numerals, and, to not unduly encumber the figures, some elements may not be indicated on some figures if they were already identified in one or more preceding figures. It should also be understood herein that the elements of the drawings are not necessarily depicted to scale, since emphasis is placed upon clearly illustrating the elements and structures of the present embodiments.

The terms "a", "an" and "one" are defined herein to mean "at least one", that is, these terms do not exclude a plural number of elements, unless stated otherwise. It should also be noted that terms such as "substantially", "generally" and "about", that modify a value, condition or characteristic of a feature of an exemplary embodiment, should be understood to mean that the value, condition or characteristic is defined within tolerances that are acceptable for the proper operation of this exemplary embodiment for its intended application.

In the present description, the terms "connected", "coupled", and variants and derivatives thereof, refer to any connection or coupling, either direct or indirect, between two or more elements. The connection or coupling between the elements may be mechanical, physical, optical, operational, electrical, wireless, or a combination thereof.

In the present description, the terms "light" and "optical", and any variants and derivatives thereof, are intended to refer to electromagnetic radiation in any appropriate region of the electromagnetic spectrum and are not limited to visible light. For example, in one embodiment, the terms "light" and "optical" may encompass electromagnetic radiation with a wavelength ranging from about 350 to 900 nm. More particularly, although some embodiments of the present techniques can be useful in visible range applications, other embodiments could additionally or alternatively operate in other regions of the electromagnetic spectrum, for example in the millimeter, terahertz, infrared and ultraviolet regions.

It will be appreciated that positional descriptors indicating the position or orientation of one element with respect to another element are used herein for ease and clarity of description and should, unless otherwise indicated, be taken in the context of the figures and should not be considered limiting. It will be understood that spatially relative terms (e.g., "outer" and "inner", and "top" and "bottom") are intended to encompass different positions and orientations in use or operation of the present embodiments, in addition to the positions and orientations exemplified in the figures.

The expressions "illuminating beam" and "resulting light" are used throughout the description. The expression "illuminating beam" refers to light which is sent towards the soil under investigation. The expression "resulting light" refers to light emanating from the soil after its irradiation by the illuminating beam. The resulting light can include light that has not been absorbed by the sample or light scattered and/or reflected by the sample. The resulting light could be, in some context, the result of various physical processes (e.g., luminescence, photoluminescence, fluorescence, phosphorescence, and the like). Hence, the resulting light is the light emanating from the soil after the interaction between the illuminating beam and the soil.

The term "field" is herein used to refer to a region of land where trees, plants, crops and the like usually grow. The term "soil" is herein used for qualifying s the underground area beneath the surface of the field, which may include the surface or a portion thereof.

Optical Probe

Generally described, there is provided an optical probe for analysing a soil located in an underground area of a field using spectroscopy. The optical probe allows to assess in real time, or near real time, different characteristics of the soil, which are globally referred to as "the soil condition". These characteristics include but are not limited to level of nutrients present in the soil, temperature, moisture, pH, level of organic matter and ionic concentration of the soil solution.

The optical probe can be inserted in the underground area of the field to measure and monitor the soil condition in situ, without the need to extract a soil sample from the field prior to its characterization, thereby allowing to obtain a dynamic characterization of the soil, instead of a single static measurement of the soil condition, which is typically obtained in a laboratory. In some embodiments, this dynamic characterization can be, in turn, used to plan the maintenance of the field, plan the fertilization of the filed, evaluate and potentially prevent the risk of diseases for the tree(s), plant(s) and/or crop(s) growing in the field. Furthermore, by its size and configuration, the optical probe can also be moved from one location to another to take measurements at different locations of the field being characterized, thereby allowing to obtain a global representation (i.e., a "cartography") of the field. The optical probe also outputs measurements having a relatively high spatial precision.

The optical probe could be used to characterize different substrates such as, and without being limitative, compost, manure, food, and/or plants. Of course, these examples are nonlimitative and serve an illustrative purpose only.

As it has been previously mentioned, the optical probe relies on spectroscopy, i.e., the production and investigation of spectra for determining the soil condition. The spectra are collected after the irradiation of the soil (or a portion thereof) with light.

Now turning to the Figures, different embodiments of the optical probe, as well as methods of using the same will be described.

Referring to FIGS. 1 to 7, embodiments of an optical probe 20 for analysing a soil located in an underground is illustrated. The optical probe 20 includes a light source 22, a probe head 24 and a detector 26, which will now be respectively described in greater detail.

Light Source

Figure 2:
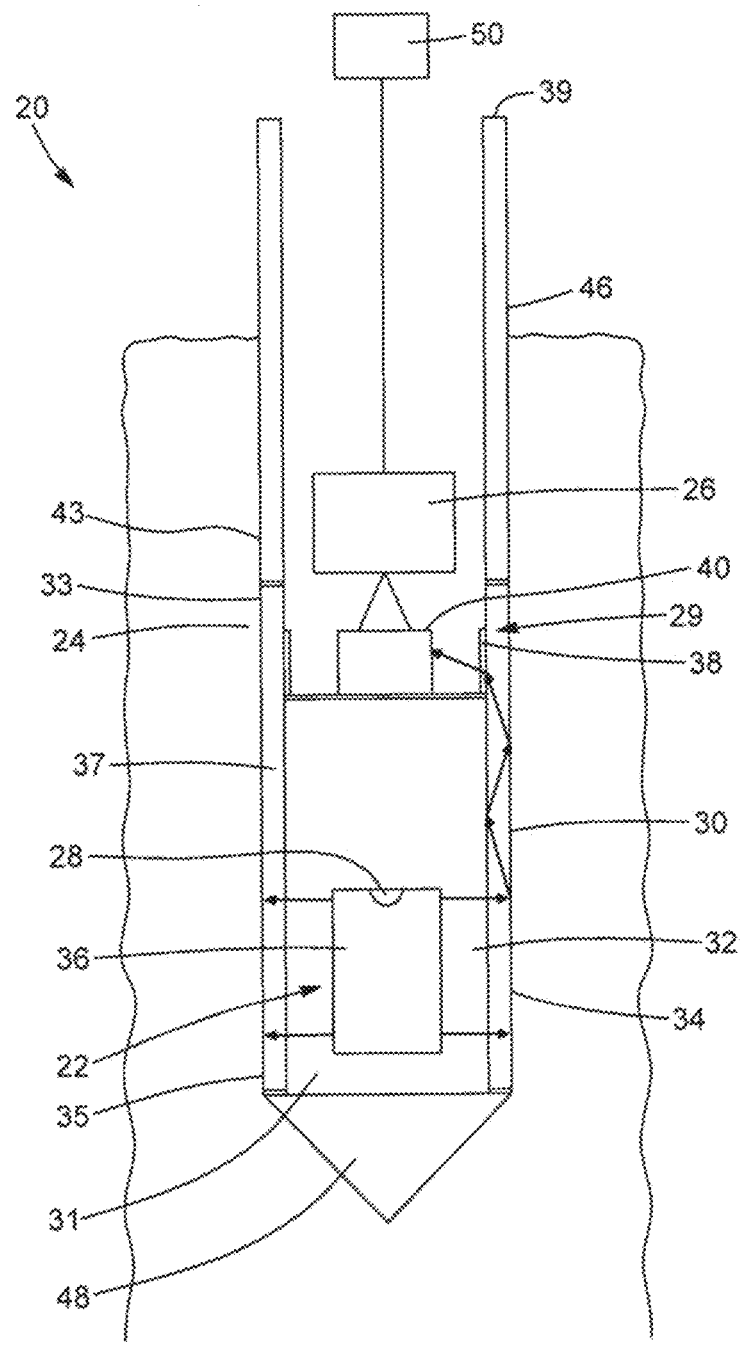
FIG. 2 is an enlarged side view of a probe head, in accordance with one embodiment.
Figure 3:
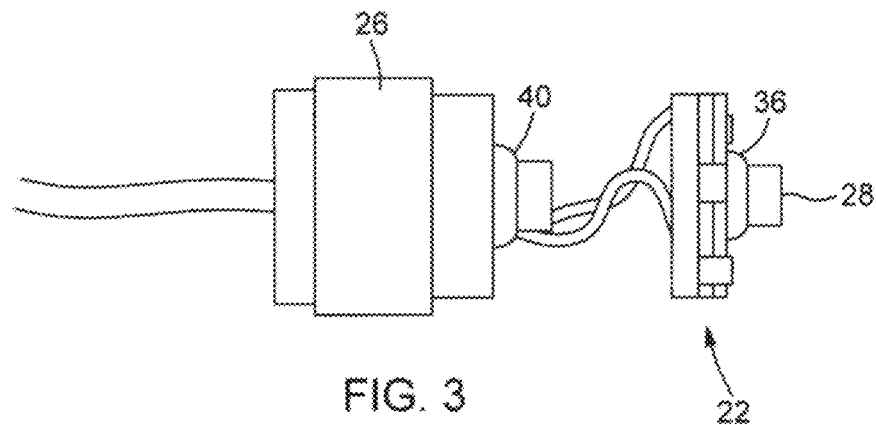
FIG. 3 is a representation of a light source and a detector, in accordance with one embodiment.
Figure 4:
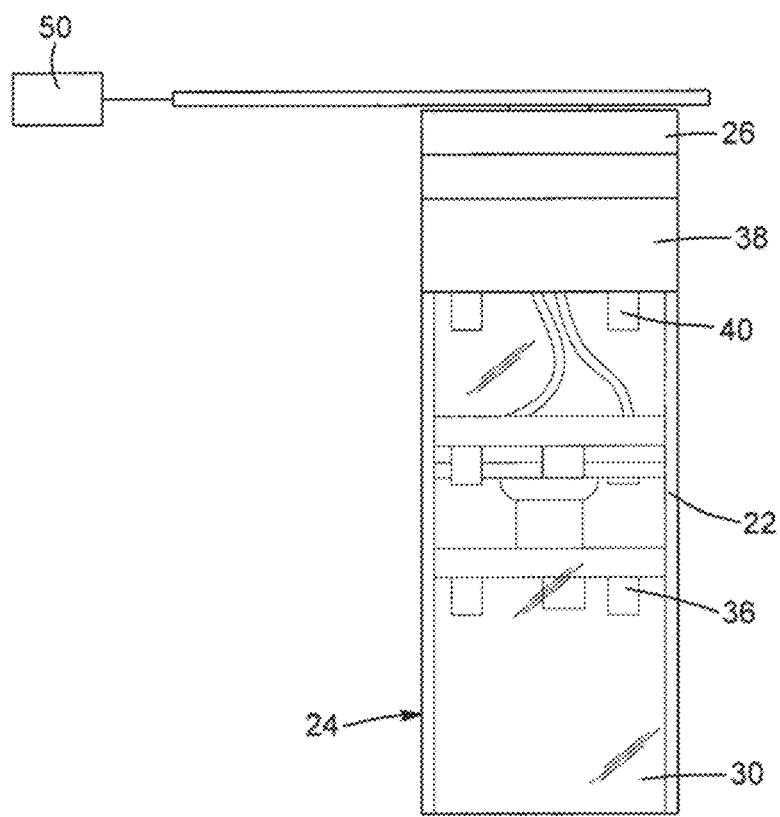
FIG. 4 is a partial view of a probe head, in accordance with one embodiment.
Figure 5:
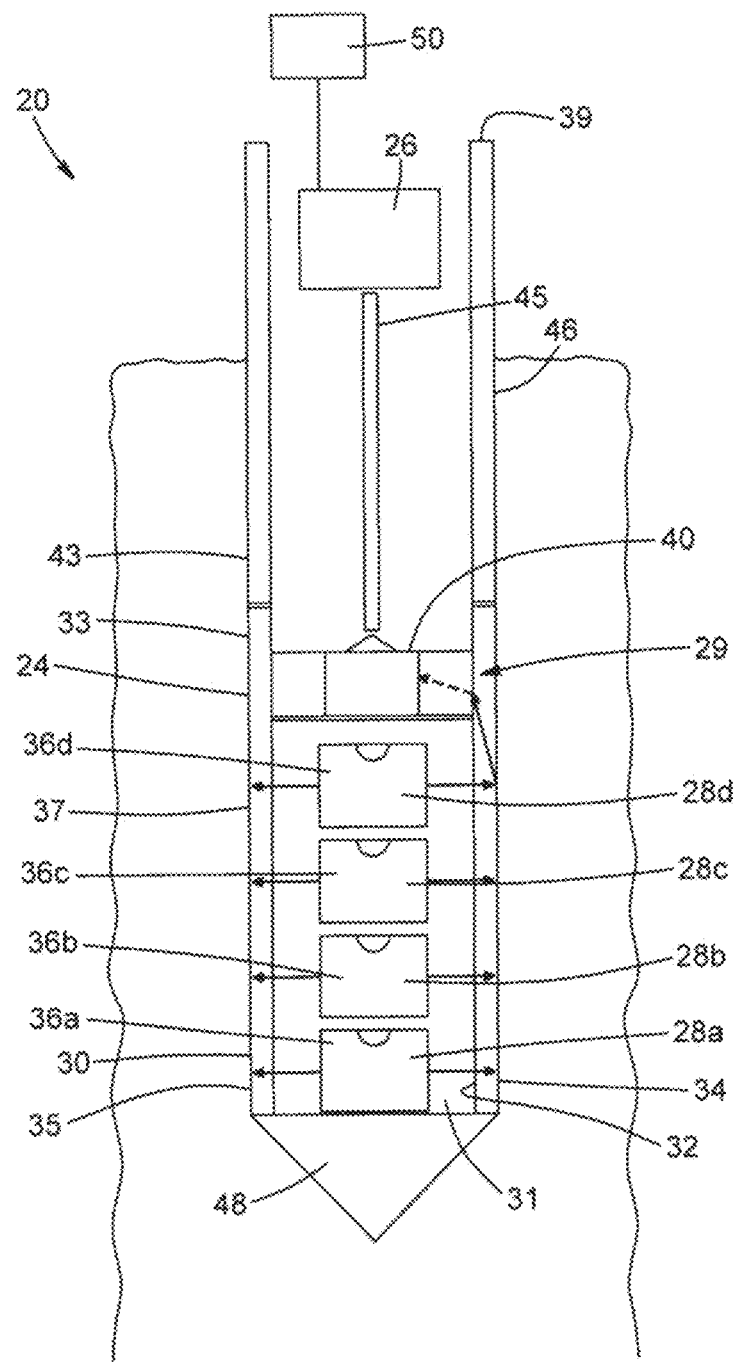
FIG. 5 is an enlarged side view of a probe head, in accordance with another embodiment.
Figure 6:
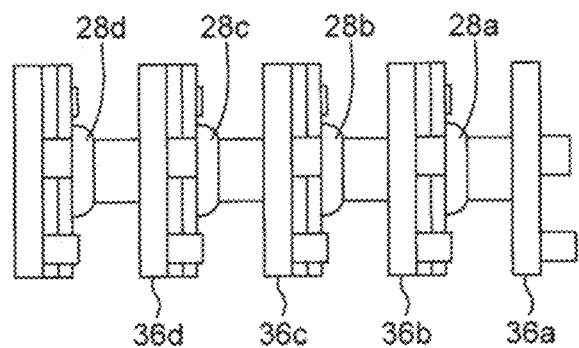
FIG. 6 is a representation of a light source, in accordance with one embodiment.
Figure 7:
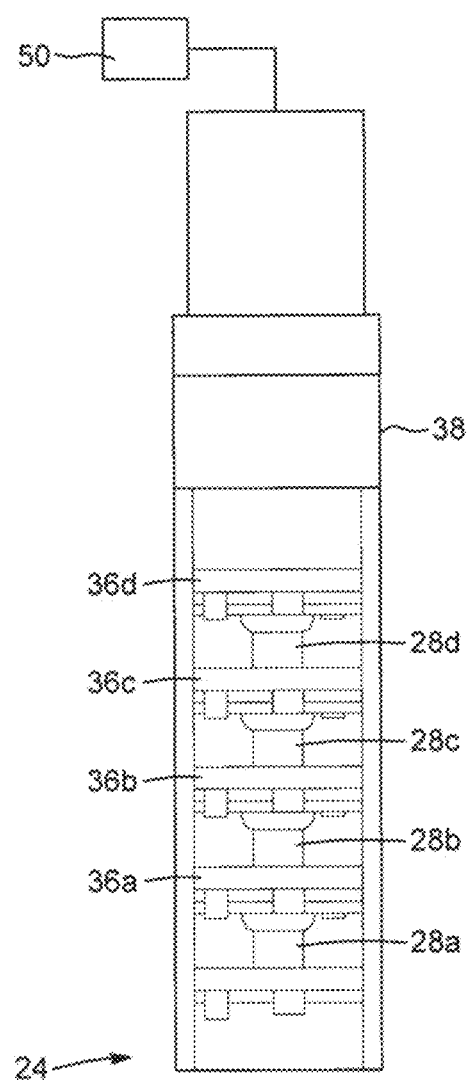
FIG. 7 is a representation of the light source illustrated in FIG. 6, inserted in a probe head, in accordance with one embodiment.

Different configurations of the light source 22 can be used in the optical probe 20. FIGS. 2 to 4 illustrate a first embodiment of the light source 22 and FIGS. 5 to 7 illustrate a second embodiment of the light source 22. In nearly all implementations, the light source 22 is operable to generate an illuminating beam towards the soil.

In the first embodiment, illustrated in FIGS. 2 to 4, the light source 22 is embodied by one light-emitting diode (LED) 28. It has to be noted that the light-emitting diode 28 could be, for example and without being limitative, replaced by a solid-state lighting source, including lasers, organic LEDs (OLEDs), incandescent lighting, halogen lighting, fluorescent light, infrared heat emitters, discharge lighting, combinations thereof or the like.

It has to be noted that the illuminating beam has a spectral profile which can be obtained with one or more light emitters. The spectral profile can either be relatively broad, i.e., the spectral profile covers a relatively large portion of the electromagnetic spectrum, or relatively narrow, i.e., covers only one or more portions of the electromagnetic spectrum. The combination of different light sources or emitters may be useful to extend the overall bandwidth of the emission spectrum and/or to maximize the relative power of some portions of the emission spectrum. In the context of soil analysis application, different wavelengths or different wavebands can serve different purposes. For example, and without being limitative, visible, infrared and blue light can be useful for detecting level of nutrients, level of available nutrients, ionic concentration of the soil solution, temperature, moisture, pH, level of organic matter and soil texture. Ultra-violet light can be useful for fluorescent matter, mineral and/or organic.

In some embodiments, the spectral profile comprises a waveband ranging from about 350 nm to about 900 nm. In other embodiments, the spectral profile of the illuminating could comprise a visible waveband ranging from about 400 nm to about 750 nm. In the context of the first embodiment of FIGS. 2 to 4, the spectral profile of the light source 22 is obtained with a single light source.

In the second embodiment, illustrated in FIGS. 5 to 7, the light source 20 includes a plurality of LEDs (labelled 28a, 28b, 28c and 28d in FIG. 5). The illumination beam is thus obtained using a plurality of sub-sources, each emitting a respective illumination sub-beam. The sub-sources forming the light source 22 can be a stack of light-emitting diodes. The stack of light-emitting diodes includes at least one of a white broad band light-emitting diode, an infrared broad band light-emitting diode, a blue-light emitting diode and/or an ultra-violet light-emitting diode. In one implementation, the stack can include, for example and without being limitative, an ultra-violet light-emitting diode 28a, a blue light-emitting diode 28b mounted on the ultra-violet light-emitting diode 28a, an infrared light-emitting diode 28c mounted on the blue light-emitting diode 28b and a white broad band light-emitting diode 28d mounted on the infrared light emitting diode 28c. In this example, the ultra-violet light-emitting diode 28a can have a spectral profile comprising a waveband centered around 385 nm the blue light-emitting diode 28*b* can have a spectral profile comprising a waveband centered around 488 nm, the infrared light-emitting diode 28*c* can have a spectral profile comprising a waveband ranging from about 750 nm to 850 nm and the white broad band light-emitting diode 28*d* can have a spectral profile comprising a waveband ranging from about 420 nm to about 700 nm. Alternatively, the light source 22 or the sub-sources, e.g., the light-emitting diodes 28*a*-*d* could emit in the UV, the NIR region and/or the IR region of the light spectrum, depending on the soil or field under study. Each one of the light-emitting diodes 28*a*-*d* is optically coupled with a corresponding one of the radial lenses 36*a*-*d*, such that each sub-beam is collimated towards the soil and through the transparent wall 30.

The light source 22, including the single LED 28 and the stack of LEDs 28*a*-*d*, are typically configured for emitting light in a continuous regime. It will however be readily understood that the light source 22 could be operated either in a continuous regime or an intermittent regime, according to one's needs and/or the targeted application(s). One skilled in the art will readily understand that the choice and the configuration of the light source 22 may be limited and/or influenced by the predetermined parameters dictated by a given application. The predetermined parameters include but are not limited to wavelength, power, spatial profile and spectral profile.

Probe Head

Still referring to FIGS. 1 to 7, but more particularly to FIGS. 4 and 7, the probe head 24 will be described in greater detail Generally described, the probe head 24 is insertable into the underground area to contact the soil, and so, in use, the soil generally surrounds at least partially the probe head 24, and in some instances, mechanically contacts the probe head 24, or at least a portion thereof.

The probe head 24 includes a transparent wall 30 defining a hollow chamber 31 within the probe head 24. The transparent wall 30 has a top extremity 33 and a bottom extremity 35 defining an optical path 37 therebetween. The light source 22, which has been previously presented, is mounted in the hollow chamber 31. In some embodiments, the light source 22 is mounted near the bottom extremity 35 of the transparent wall 30. The light source 22 is configured to generate the illumination beam towards the soil. The illumination beam passes through the transparent wall 30 to irradiate the soil, thereby producing a resulting light emanating from the soil, as defined above. After the irradiation of the soil by the illumination beam, a portion of the resulting light returns towards the probe head 24 and is guided in the transparent wall 30 by total internal reflection along the optical path 37. In some instances, the transparent wall 30 is said to be configured for collecting and trapping the resulting light reflected by the soil, after an interaction between the illuminating beam and the soil. In some embodiments, the portion of the resulting light guided by the transparent wall comprises light scattered by the soil and/or light reflected by the soil. The transparent wall 30, which acts as a light collector, is optically transparent to the spectral profile of the illuminating beam, or at least a portion thereof (i.e., the transparent wall 30 may or may not absorb a portion of the illuminating beam). The transparent wall 30 generally includes an inner surface 32 and an outer surface 34 and extend from the top extremity 33 to the bottom extremity 35. In operation, the transparent wall 30 collects and guides the resulting light with total internal reflection. Total internal reflection occurs when a propagating wave is incident onto the boundary between two media at an angle larger than a critical angle with respect to the normal to the surface. The two media could, for example, be the soil (or a solution contained therein) and the transparent wall 30. The critical angle is the angle of incidence above which the total internal reflection occurs, i.e., the angle above which the resulting light will be guided in the transparent wall 30. The critical angle $\theta_c$ is given by Snell's law and can be written as:

$$\theta_c = \arcsin\left(\frac{n_2}{n_1}\right) \quad (1)$$

wherein $n_2$ is the refractive index of the soil (or the soil solution contained therein) that is contact with the transparent wall 30 and $n_1$ is the refractive index of the material forming the transparent wall 30.

Figure 8:
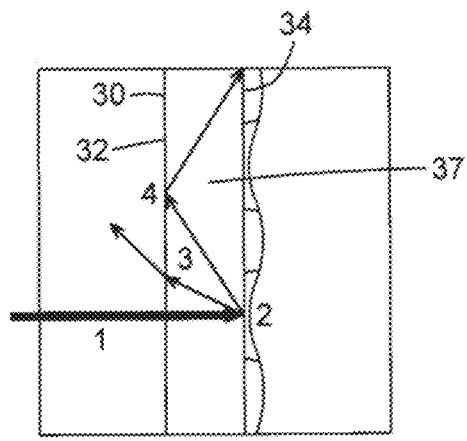
FIG. 8 is an illustration of light being guided by total internal reflection in a transparent wall included in a probe head, in accordance with one embodiment.
Figure 9A:
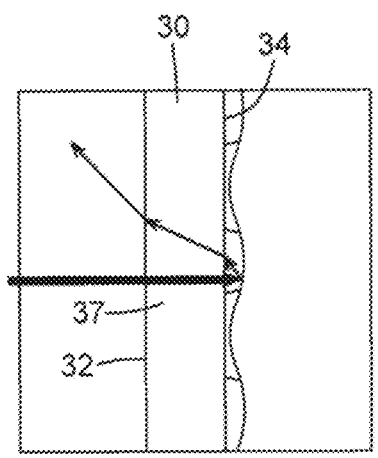
FIGS. 9A-B are illustrations of light that is not guided in a transparent wall included in a probe head.
Figure 9B:
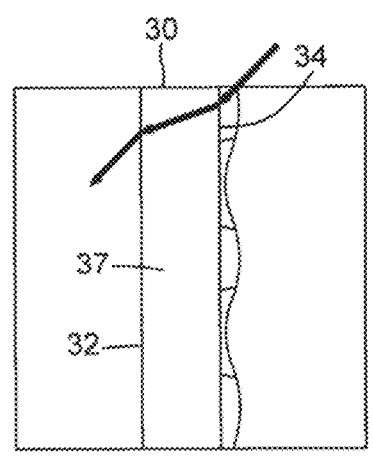

Now referring to FIGS. 8 and 9A-B, onto which a portion of the probe head 24 is shown, the illuminating beam is first illustrated as passing through the transparent wall 30 to irradiate the soil. It is to be noted that a change to the angle at which the illuminating beam intersects with the surface of the transparent wall 30 would result in a change of the proportion of light that is transmitted through the transparent wall 30, as one skilled in the art would readily understand. In one embodiment exemplified in FIG. 8, the illuminating beam, (which is labelled "1)" in FIG. 8), is collimated and perpendicularly incident to the inner surface 32 of the transparent wall 30, such that the illuminating beam is mostly transmitted therethrough. After its passage through the transparent wall 30, the illuminating beam then interacts with the soil at a point (labelled "2)" in FIG. 8. The point is illustrated as being in contact with the outer surface 34 of the transparent wall 30, but, in some instances, a relatively small distance can separate the outer surface 34 of the transparent wall 30 from the point. The interaction between the illumination beam and the soil results in the illuminating beam being scattered by the soil. It has to be noted that a portion of the illuminating beam that interacts with the soil particles can be scattered in the form of light (i.e., radiative energy) and that a portion of this light will subsequently be guided in the transparent wall 30. One would note that the scattering can either be elastic or inelastic. Another portion of the illuminating beam that interacts with the soil particles will not be scattered in the form of light but will rather be converted in another form of energy (i.e., non-radiative forms of energy). An example of non-radiative forms of energy is thermal or chemical energy. The portion of the illuminating beam converted in non-radiative energy will not be guided in the transparent wall. In some implementations, the illuminating beam is scattered in all directions or nearly all directions. The scattered or reflected light can either be collected by the transparent wall 30 or be retransmitted through the transparent wall 30. In the first scenario, the reflected light will be referred to as the "resulting light scattered or reflected by the soil". This light is collected by the transparent wall 30 and is guided therein along the optical path 37. In the second scenario, the light is not collected, and so is not guided along the optical path 37. An example of this scenario is illustrated in FIG. 8 (see for example label "3)" and in FIG. 9A. Indeed, the light is not guided by the transparent wall 30 and therefore will not be received by any detector. In the first scenario presented above, only the portion of the resulting light that satisfies the conditions for total internal reflection, i.e., having the appropriate angle, is guided and collected by the transparent wall 30, see for example the label "4)" in FIG. 8. It has to be noted that the expressions "guided", "collected" and "trapped" by transparent wall 30 could be used interchangeably, as long as it refers to the light that follows the optical path 37 between the inner surface 32 and the outer interface 34 of the transparent wall 30. It has to be noted that it is generally the light that travels from the bottom extremity 35 towards the top extremity 33 that is received at the detector, and thus analyzed, as it will be explained in greater detail later. In some embodiments, the portion of the light which is guided by the transparent wall 30 has interacted with the soil solution that is sticking to the outer surface of the transparent wall 30 or present at a relatively small distance from the transparent wall 30. As exemplified in FIG. 9B, light coming from other source(s) than the light source 22, which is sometimes referred as "optical noise", is not collected or guided by the transparent wall 30. Moreover, it is to be noted that the specular reflections of the illuminating beam on the inner surface 32 and the outer surface 34 of the transparent wall 30 are typically not collected or guided by the transparent wall 30.

In the illustrated embodiment, the optical probe 20 also includes a body 46 made of, for example and without being limitative, a tube 39 (see for example FIG. 1). The tube 39 typically has two end portions: a top end portion 41 and a bottom end portion 43. The top end portion 41 could be provided with handles, or similar structure, near or at its extremity, to help the user inserting the optical probe 20 into the ground or removing the optical probe 20 from the ground. The top end portion 41 usually refers to the portion of the tube 39 (or the body 46) being exposed to ambient air when the optical probe 20 is inserted in the ground for analysis, while the bottom end portion 43 usually refers to the portion of the tube 39 (or the body 46) being exposed to the underground area. The probe head 24, and more particularly the transparent wall 30, is typically mounted and/or affixed to the bottom end portion of the tube 39. Other details regarding the body 46 will be provided later.

As depicted in the illustrated embodiments, the transparent wall 30 forms a tubular hollow chamber, i.e., the transparent wall 30 substantially defines the shape of a cylinder. The hollow chamber 31 is generally filled with air or with pure nitrogen and is confined by the inner surface 32 of the transparent wall 30. The pure nitrogen can be useful in order to reduce or eliminate condensation in the hollow chamber 31. It is to be noted that the outer surface 34 of the transparent wall 30 could be referred to as "an outer cylindrical periphery".

The inner surface 32 and the outer surface 34 of the transparent wall 30 are relatively "smooth", i.e., their surface roughness is such that it does not have significant effects on the optical properties of the transparent wall 30. In some embodiments, the inner surface 32 and/or the outer surface 34 could be coated with an additional layer or treated with an appropriate physical or chemical process, for example and without being limitative, for enhancing predetermined optical properties of the transparent wall 30, such as the reflexivity or the transmissivity of light. The transparent wall 30 is made from a material impermeable to the soil solution present in the soil, i.e., the soil solution cannot diffuse within the hollow chamber 31 and so does not penetrate the probe head 24. As such, the transparent wall 30 is generally made from a non-porous material, or the porosity of the material is such that the soil solution stays outside of the probe head 24.

The thickness of the transparent wall 30 can be from about 2 mm to 5 mm, wherein the thickness is measured between the inner surface 32 and the outer surface 34. The transparent wall 30 is typically made from a single material or alloy (i.e., forms a monolithic and continuous piece of material). Alternatively, the transparent wall 30 could be made of a plurality of interconnecting pieces.

While the transparent wall 30 can, in some embodiments, forms a tube, e.g., when the probe head 24 is tubular, it could also take the shape of any other variants of a cylindrical component, i.e., any shapes having a longitudinal dimension substantially greater than a transverse dimension or being substantially narrow.

In the illustrated embodiments, the cross-section of the probe head 24 is substantially circular, but one would readily understand that the shape of the cross-section may change, and may include other rounded shapes, such as and without being limitative, ellipse, bubble, globe, hemisphere or rounded polygons. The shape of the probe head 24 could vary to include non-rounded shapes, e.g., parallelepiped, polygon, combinations and/or variants thereof, or any other shapes As for its positioning, the probe head 24, and in some instances, the transparent wall 30, are typically fixed near or at the extremity of the bottom end portion 43 of the tube 39 forming the body 46. More particularly, if the extremity of the bottom end portion 43 of the tube 39 is open (i.e., provided with a hole) a portion of the transparent wall 30 can be slidably inserted and engaged therein (i.e., in the open extremity of the bottom end portion 43 of the tube 39). It is to be noted that supplementary fixing components or devices could be used to maintain the transparent wall 30 secured to the extremity of the bottom end portion 43 of the tube 39, such as buttons, snaps, screws, glue, tape, welding, slits, guiding rails, combinations thereof, or any other components and/or means which would allow the transparent wall 30 to be affixed to the tube 39.

In other embodiments, the bottom end portion 43 of the tube 39 and/or a region near its extremity could be threaded in its inner portion, and, similarly, a portion of the transparent wall 30 or a piece mounted near the top extremity 35 of the transparent wall 30 could also be threaded on its outer portion, such that the transparent wall 30 or the piece mounted near the top extremity 33 of the transparent wall 30 could be screwed (i.e., secured after a rotation) to the extremity of the bottom end portion 43 of the tube 39.

Now turning to the dimensions of the transparent wall 30, the transparent wall 30 could form, for example and without being limitative, a tube having an outside diameter of about 2.5 cm and a height (i.e., a longitudinal dimension measured between the top extremity 33 and the bottom extremity 35) of ranging between about 0.5 cm and about 5 cm. Of course, the dimensions of the nominal diameter, the outside diameter and length of the light collector, depending on the surface required for the analysis, as well as other parameters (e.g., the depth of the soil at which the analysis is conducted).

The probe head 24 can have an outer surface area ranging from about 400 $mm^2$ to about 4000 $mm^2$. In some embodiments, the outer surface area of the transparent wall 30 ranges from about 400 $mm^2$ to about 4000 $mm^2$.

In some embodiments, the optical probe 20 allows an isotropic measurement of the soil and provides a 360°-characterization around the probe head 24 (i.e., the optical probe 20 provides a view of the soil or the soil solution surrounding the transparent wall 30), which is enabled by the 360 rotational degrees of symmetry of the tube.

As it has been previously mentioned, the hollow chamber 31 is typically filled with air or nitrogen. As such, the refractive index of the hollow chamber 31 can correspond to the refractive index of air (i.e., about 1). For the light to be trapped within the transparent wall 30, the material forming the transparent wall 30 should have an index of refraction higher than the index of refraction of air (i.e., the refractive index of the hollow chamber 31 is different than the refractive index of the material forming the transparent wall 30). For example, and without being limitative, the refractive index of the transparent wall 30 could range from about 1.4 to 1.8. In some embodiments, the refractive index of the transparent wall 30 is about 1.45. In other embodiments, the refractive index of the transparent wall 30 is about 1.77.

In some embodiments, the optical probe 20 include a first radial lens 36 optically coupled to the light source 22 for generating a collimated illuminating beam. The first radial lens 36 has a substantially cylindrical body and is concentrically mounted within the transparent wall 30, in the hollow chamber 31. In one embodiment, an outer periphery of the first radial lens 36 is in contact with the inner surface 32 of the transparent wall 30. Alternatively, the first radial lens 36 could be mounted in a concentric manner with respect with the transparent wall 30, but a relatively small gap could be maintained between the first radial lens 36 and the transparent wall 30, so that the outer periphery of the radial lens 36 is not in contact with the inner surface 32 of the transparent wall 30. As it has already been mentioned, the first radial lens 36 is optically coupled to the light source 22 and is generally located at the output of the light source 22. Such a positioning allows to generate the collimated illuminating beam through transparent wall 30 to irradiate the soil. In some embodiments, for example when the probe head 24 is tubular, the first radial lens 36 can generate light towards the outer cylindrical periphery of the probe head 24. In some embodiments, the collimated illuminating beam is generated in a radial direction, i.e., from a central portion of the probe head 24 towards the outer surface 34 of the transparent wall 30.

As it has been previously described, the transparent wall 30 is generally made of a material optically transparent to the spectral profile of the illuminating beam. The optically transparent material can also have other properties, such as being resistant to abrasion. A broad variety of materials could be used, for example and without being limitative: clear fused quartz, quartz, sapphire, other types of glass and acrylic. Broadly, any optical materials configured for guiding light can included in the transparent wall 30.

As better illustrated in FIGS. 2 and 5, the optical probe 20 includes an optical element 29 mounted in the hollow chamber 31, near or at the top extremity 33 of the transparent wall 30. The optical element 29 is configured to guide the portion of the resulting light guided in the transparent wall 30 from the transparent wall 30 to the detector 26. In some embodiments, the optical element 29 comprises an optical diffuser 38 positioned near or at the top extremity 33, in the hollow chamber 31. The optical diffuser 38 is optically coupled with the transparent wall 30 for scattering the portion of the resulting light guided in the transparent wall 30 inside the probe head 24. In some embodiments, such as the one illustrated in FIG. 10C, the optical diffuser 38 has the shape of a cone and is made from silicone. Such an implementation of the optical diffuser 38 will be referred to as a cone-shaped optical diffuser. As illustrated, the bottom portion of the cone-shaped optical diffuser is in mechanically contact the top extremity 33 of the transparent wall 30, which allows the optical coupling between the transparent wall 30 and the cone-shaped optical diffuser. In the illustrated embodiment, the cone-shaped optical diffuser is optically coupled with the detector 26 with an optical fiber 45.

Figure 10A:
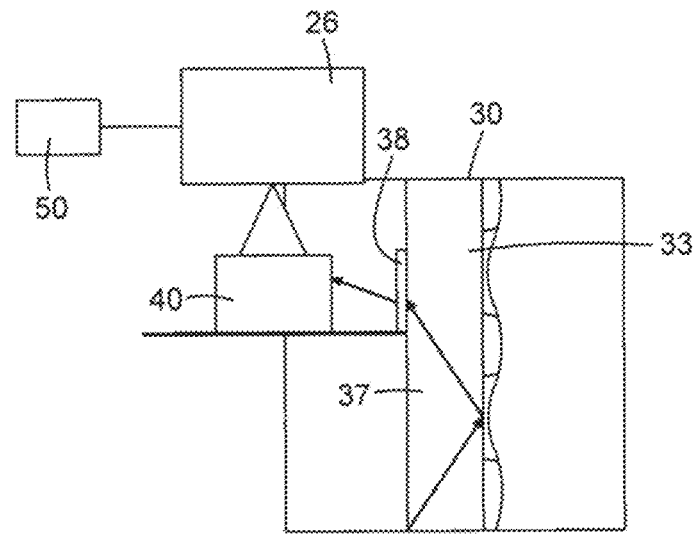
FIGS. 10A-D show different embodiments for detecting the light guided by total internal reflection in a transparent wall included in a probe head.
Figure 10B:
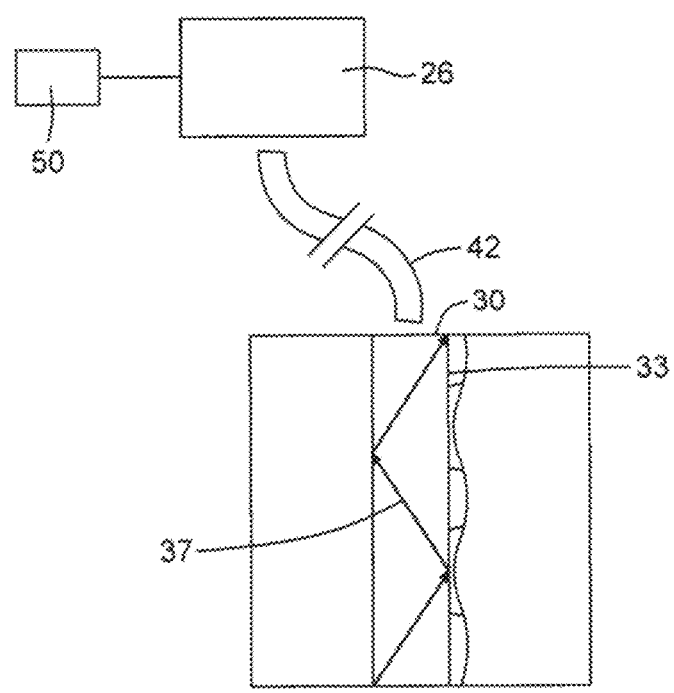
Figure 10C:
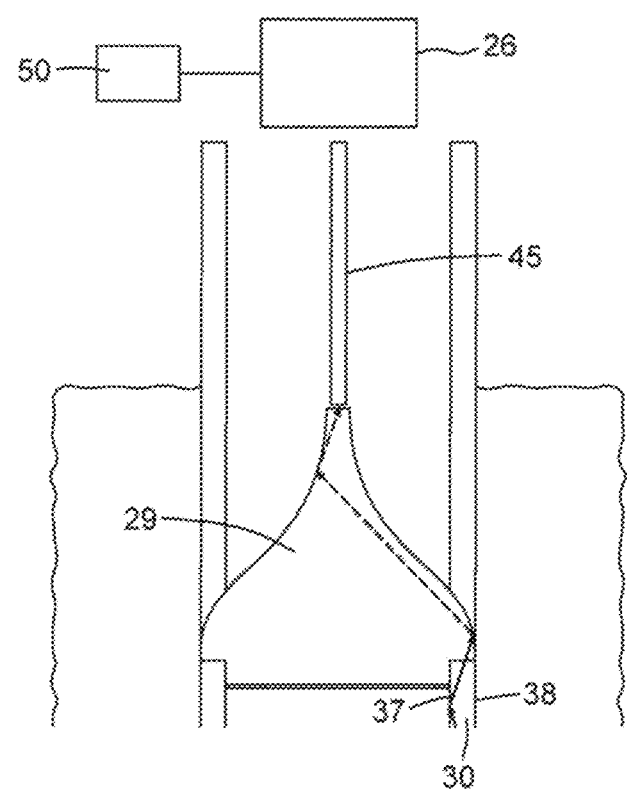
Figure 10D:
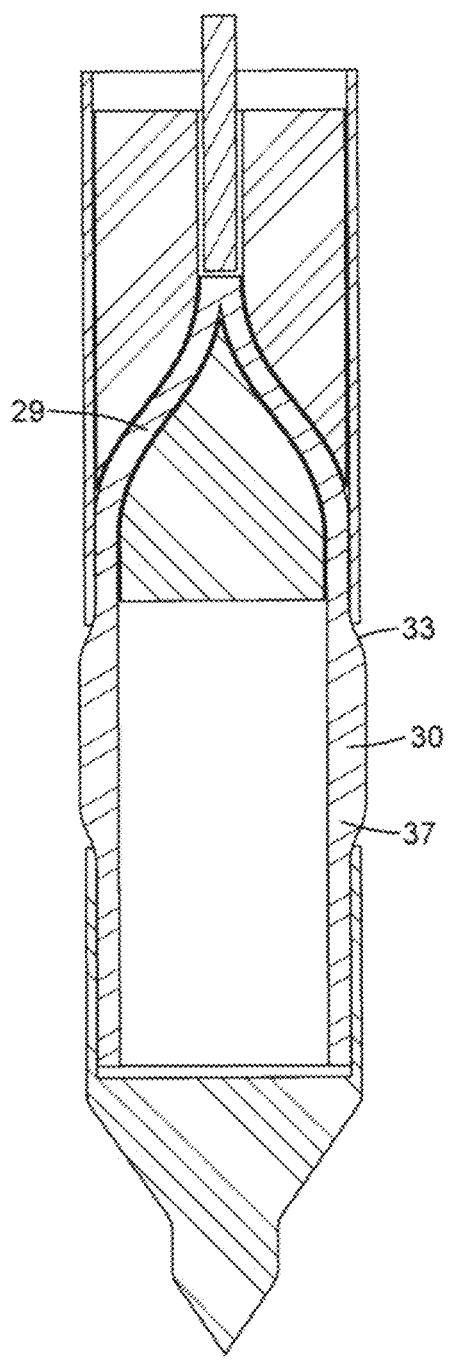

In other embodiments, such as the one illustrated in FIG. 10D, the optical element 29 could be a transparent optical guide, extending from the top extremity 33 of the transparent wall 30 to the detector.

In some embodiments, such as the ones illustrated in FIGS. 2 and 5, the optical probe 20 can also include a second radial lens 40, similar to the first radial lens 36 that has been previously described. The second radial lens 40 can also have a substantially cylindrical body and can be concentrically mounted within the transparent wall 30, in the hollow chamber 31, e.g., an outer periphery of the second radial lens 40 can be in contact with the inner surface 32 of the transparent wall 30. Alternatively, the second radial lens 40 could be mounted in a concentric manner with respect with the transparent wall 30, but a relatively small gap could be maintained between the second radial lens 40 and the transparent wall 30. The second radial lens 40 is configured to receive the scattered light and focusing the scattered light towards the detector 26, with or without the intermediate of an optical component (e.g., an optical fiber 45, such as the one illustrated in FIG. 10C can be provided between the second radial lens 40 and the detector 26), as it will be described with greater detail herein below. In some embodiments, the second radial lens 40 receives light at its radial outer periphery and focuses the same such that the incoming light is focused towards the detector 26.

In some implementations, the optical diffuser 38 can be replaced by an optical material, such as, for example and without being limitative, optically clear epoxy or a resin matrix having air bubbles therein, as illustrated in FIG. 5. Such an optical material could be in contact or even connect the inner surface 32 of the transparent wall 30 with the second radial lens 40. In one exemplary embodiment, the resin matrix has an aperture in its center to allow the insertion second radial lens 40 in the aperture.

In some embodiments, one or more optical component(s) can be provided between the second radial lens 40 and the detector 26. For example, and without being limitative, an optical fiber 45 can be provided between the second radial lens 40 and the detector 26. This embodiment is illustrated in FIGS. 5 and 10. Other optical elements affecting the light being guided from the second radial lens 40 to the detector 26 can be provided. Such optical elements include, but are not limited to lenses, mirrors, filters, and other suitable reflective, refractive and/or diffractive optical components.

In some embodiments, such as the one illustrated in FIG. 10A, the optical diffuser 38 conforms with the inner surface 32 of the transparent wall 30, which can be, for example and without being limitative, an inner portion of the probe head 24, such as the inner surface 32 of the transparent wall 30. Alternatively, the optical diffuser 38 could also be a diffusing surface, or a coating of paint (or any other diffusing material applicable to a glass material).

In other embodiments, the optical probe 20 further comprises at least one optical fiber 42 for guiding the portion of the resulting light guided by the transparent wall 30 form the transparent wall 30 towards the detector 26, as depicted in the illustration of FIG. 10B. The optical fiber 42 can be in mechanical contact with the transparent wall 30 or a portion thereof. In such embodiments, the transparent wall 30 can be provided with at least one hole for receiving the optical fiber 42 therein. Such a hole can be provided near or at the top extremity 33 of the transparent wall 30. More particularly, the hole could be provided in a solid portion of the transparent wall 30 and extends in a direction parallel to a longitudinal axis of the transparent wall 30, i.e., such that the input of the optical fiber is aligned within the longitudinal axis of the transparent wall 30. In that scenario, the optical fiber 42 is placed in the optical path 37. The hole can be deep enough that the optical fiber could be inserted and maintained in place with or without affixing means. This configuration allows the optical fiber to collect the resulting light being guided in the transparent wall 30. Typically, each hole is sized and configured to receive one optical fiber. It is to be noted that the optical fiber(s) 42 could also be attached to the transparent wall 30 using appropriate fixing and/or sticking means.

In some embodiments, an additional layer made of, for example and without being limitative, a silver-based material, aluminum, or any other reflective coating(s) may be provided on the inner surface 32 and/or the outer surface 34 of the transparent wall 30. In some scenarios, the use of such a reflective coating could increase the signal produced by the detector 26. Indeed, if the transfer of light is more efficient, as it could be the case when an additional layer made of a reflective coating is provided, the detector 26 can receive more light, and therefore produces a stronger signal.

In some embodiments, the probe head 24 encloses at least one of the light source 22 and the detector 26, i.e., at least one of the light source 22 and the detector 26 is mounted in the hollow chamber 31. In some embodiments, the light source 22 and the detector 26 are enclosed in hollow chamber 31.

It is to be noted that the light source 22, the probe head 24 and/or the detector 26 could be coupled to optical components (not shown) configured to alter at least some of the properties of the light prior or after its interaction with the soil under investigation. The expression "optical components" herein refers, but is not limited to lenses, mirrors, filters, and other suitable reflective, refractive and/or diffractive optical components. It is to be noted that the relative position of the light source 22, the probe head 24 and/or the detector 26 may also be adjustable.

Detector

Now turning to FIGS. 10A-D, different embodiments of the detector 26 and different configurations of the detector 26 will now be described.

Generally, the detector 26 is configured to receive the portion of the resulting light guided in the transparent wall 30. Upon reception of the portion of the resulting light guided in the transparent wall 30, the detector 26 then outputs or produces an output signal representative of at least one characteristics of the soil. As previously mentioned, the characteristics of the soil are globally referred as the soil condition, and could include many different properties, such as the ones which have been previously described.

In some embodiments, the detector 26 is a light detector. An example of a light detector is a spectrometer, i.e. a device to measure the spectral properties of the portion of the resulting light guided in the transparent wall 30. The detector 26 is generally responsive in the region of operation of the light source 22, i.e., the detector 26 is sensitive to at least a portion of the wavelengths included in the spectral profile of the light source 22. However, it will be readily understood that the detector 26 is sensitive to at least a portion of the wavelength included in the spectral profile of the portion of the resulting light guided in the transparent wall 30. In some embodiments, the portion of the resulting light guided in the transparent wall 30 could be the result of various physical processes, for example and without being limitative fluorescence, luminescence, phosphorescence, photoluminescence, and the like. In some instances, appropriate filter(s) could be provided along the optical path 37 or between the components of the optical probe 20 in order to exploit one or more of the aforementioned physical processes.

Figure 13A:
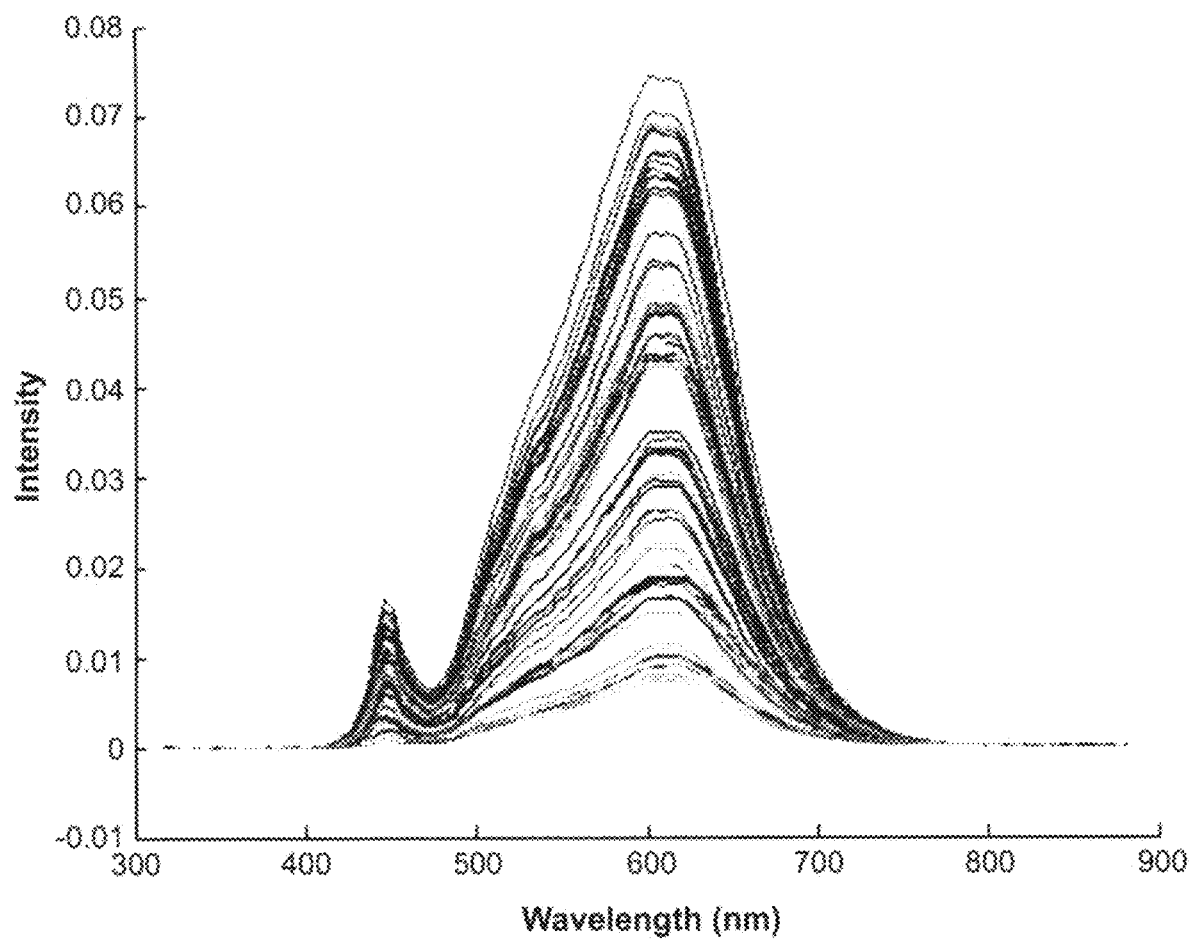
FIGS. 13A-B are examples of spectral data that can be obtained with the optical probe.
Figure 13B:
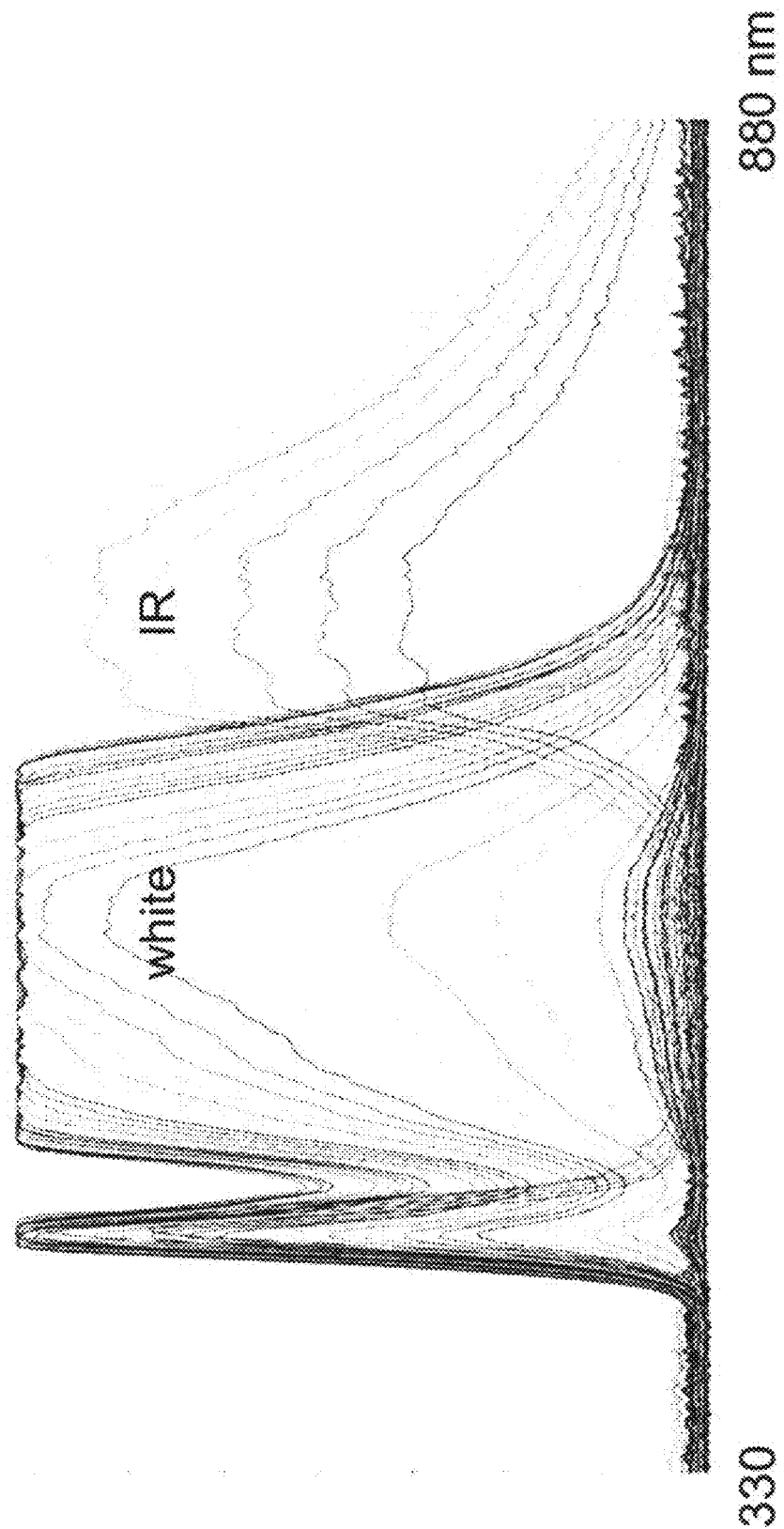

Once received by the detector 26, the resulting light may be converted to an electrical signal, electrical data and/or any other type of data using techniques already known by one skilled in the art. In some embodiments, the optical probe 20 further includes a processor 50. The processor 50 is configured to receive the output signal representative of said at least one characteristic of the soil and determine a spectral content of the portion of the resulting light guided by the transparent wall 33. In one embodiment, the processor 50 is an external computer. The external computer can be operatively connected to the optical probe 20, either wirelessly or through physical connection, and can be configured for performing at least one of the following operations: sending instructions to the optical probe 20 or one of its components (e.g., the light source 22 or the detector 26), receiving data from the optical probe 20, controlling different parameters of the optical probe 20, treating the collected data and/or generating visual representations (e.g., graph) of the soil conditions. An example of visual representation of the soil condition is illustrated in FIG. 13A, which illustrates a wavelength-dependent measurement of the soil at different measurements points. The general principles underlying such operations are generally well known to one skilled in the art but could of course be adapted in view of a particular targeted application. FIG. 13B illustrates similar measurements, but obtained with a plurality of LEDs.

As it will be readily understood, the processor 50 can be implemented as a single unit or as a plurality of interconnected processing sub-units. Also, the processor can be embodied by a computer, a microprocessor, a microcontroller, a central processing unit, or by any other type of processing resource or any combination of such processing resources configured to operate collectively as a processor. The processor 50 can be implemented in hardware, software, firmware, or any combination thereof, and be connected to the various components of the spectral identification system via appropriate communication ports.

Electrical Circuit and Power Unit

Figure 11A:
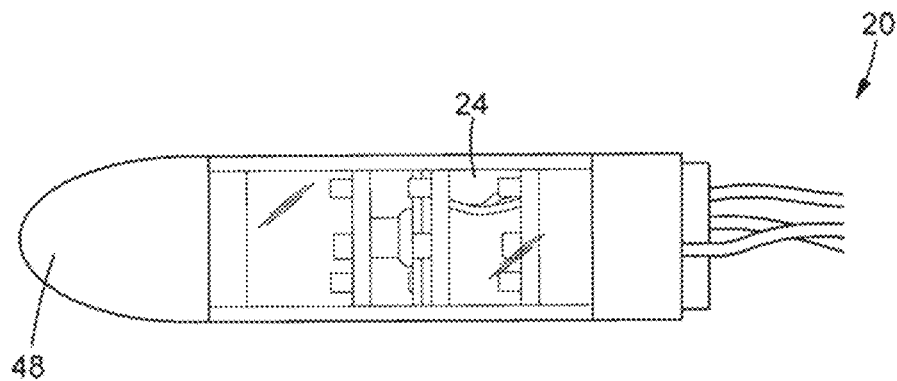
FIGS. 11A-D represent a probe head being assembled to remaining portions of the optical probe, in accordance with one embodiment.
Figure 11B:
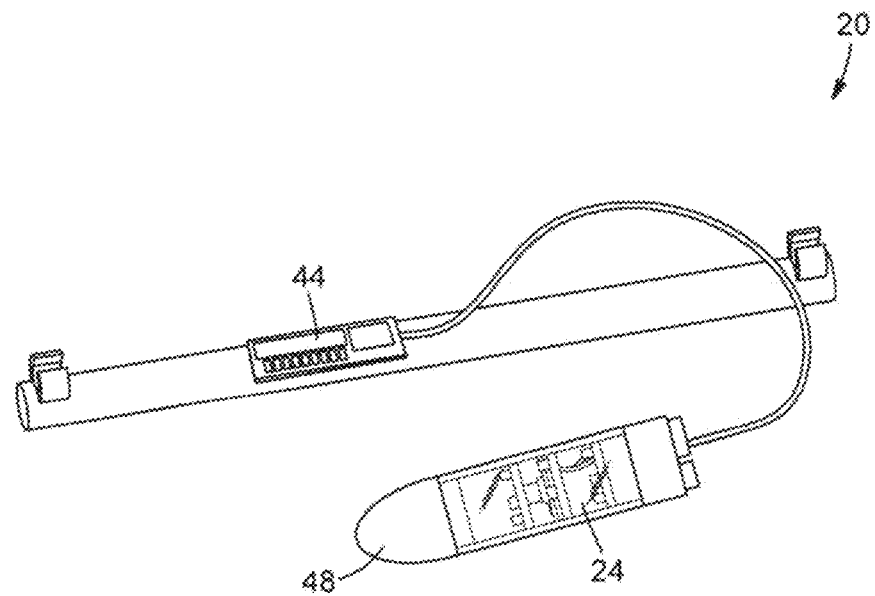
Figure 11C:
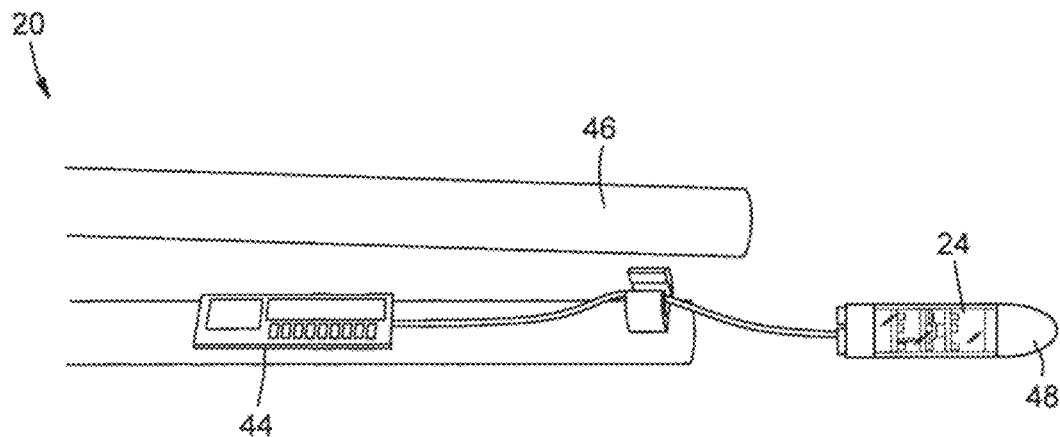
Figure 11D:
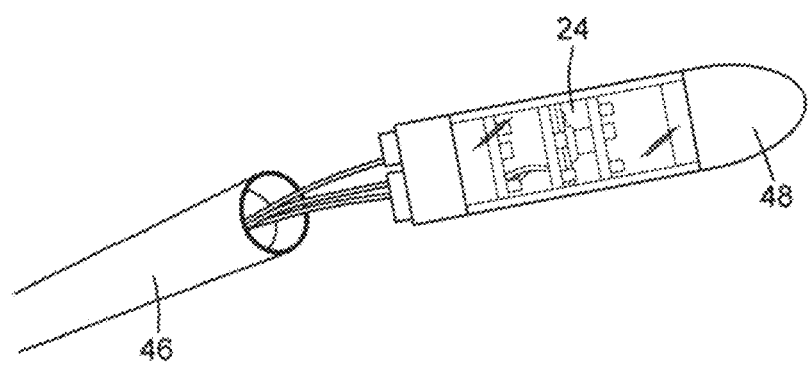
Figure 12A:
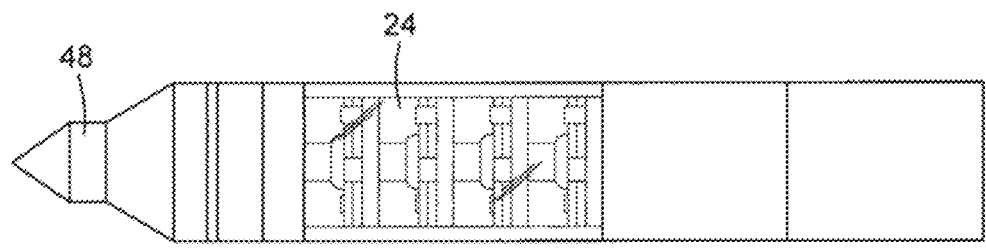
FIGS. 12A-B represent a probe head being assembled to remaining portions of the optical probe, in accordance with one embodiment.
Figure 12B:
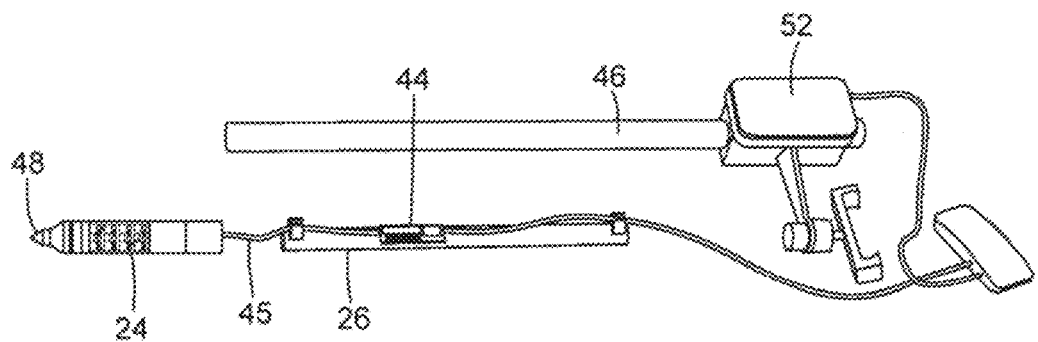

With reference to FIGS. 11A-D and 12A-B, two embodiments of the optical probe 20 being assembled are illustrated. The first embodiment is illustrated in FIGS. 11A-D and the second embodiment is illustrated in FIGS. 12A-B.

In the two embodiments, the optical probe 20 is provided with an electrical circuit 44 for powering the light source 22 and the detector 26. The design and configuration of the electrical circuit 44 may vary according to the targeted application, but could include appropriate electronics components, such as for example and without being limitative resistors, switches, amplifiers, filters, diodes, transistor, and/or any other components already known by one skilled in the art.

The optical probe 20 can also include a control unit for operating and controlling at least one of the light source 22 and the detector 26 through the electrical circuit 44. The control unit can be connected or part of the processor 50. Alternatively, the control unit of the optical probe 20 could also be operatively connectable to a computer, a smartphone, or any other type of portable devices.

In some embodiments, the optical probe 20 includes a power unit 52 for powering the electrical circuit 44. For example, and without being limitative, the power unit could include at least one battery. In some embodiments, the battery has a cycle life of about 1500 measurements.

Body

Now turning to FIGS. 11C-D and 12B, the body 46 will now be described in greater detail. The body 46 is sized and configured to receive the electrical circuit 44 therein. In some embodiments, the body 46 has a hollow portion or is at least partially hollow and houses the electrical circuit 44. The probe head 24 can also be mounted to the bottom end portion 43 of the body 46, i.e., the extremity that is the closest to the ground. As it has been previously described, at least a portion of the probe head 24 can be engaged with or mounted to the body 46.

In some embodiments, the body 46 has a height of ranging from about 30 cm to about 100 cm and the probe head 24 has a height ranging from about 0.5 cm to about 5 cm. In such embodiments, the optical probe 20 has a total height of about 35 cm. In some embodiments, the height of the body 46 can be adjustable, e.g., the height of the body 46 can be retractable In some embodiments, the optical probe 20 includes a sensing tip 48 provided near or at an extremity of the probe head 24. The sensing tip 48 can be configured to measure at least one of the properties of the soil, such as for example and without being limitative, the electroconductivity, the pH of the soil and/or any other properties which can be sensed with the sensing tip 48.

In some embodiments, the bottom extremity of the optical probe 20 is tapered (i.e., the end of the probe head 24 may reduce in diameter or thickness towards an extremity of end of the probe head 24) The bottom extremity of the optical probe 20 is typically configured, sized and positioned to allow the optical probe 20 to be inserted to the ground. In some implementations, the optical probe 20 could include a helicoidal end part configured to enter the ground when being pushed towards the ground and rotated about a rotation axis, so that the probe head 24 is exposed to the soil in the underground area. In such embodiments, the helicoidal end part has a dimension and mechanical properties which allow sufficient engagement of the optical probe 20 with the ground, thus providing stability to the optical probe 20, when inserted into the soil. In some embodiments, the optical probe 20 can be inserted at two different depths, e.g., about 15 cm and about 30 cm. Of course, one would have readily understood that the optical probe 20 can be inserted at any depth in the field. For example, and without being limitative, the probe head 24 can be inserted at a depth ranging from about 0 cm to about 80 cm under the soil surface.

In some embodiments, the bottom extremity of the optical probe 20 may be made from different materials. By way of an example, the extremity of the optical probe could be made from epoxy resin, acrylonitrile butadiene styrene (ABS) plastic, polylactic acid (PLA) plastic, aluminum or any other suitable materials.

The body 46 can be made from a broad variety of material. For example, and without being limitative, the body 46 may be made from any solid material such as polymers, including but not limited to limitative vinyl, fiberglass and rigid polyvinyl chloride (PVC), metals and metal alloys, including but not limited to aluminum and aluminium alloys, stainless steel, brass, copper, combinations thereof, or any other material that can be used to house the circuits 44 and to which the probe head 24 can be mounted. Of course, the body 46 can have various geometrical configurations (i.e., size and dimensions). As depicted however, the body 46 has a cylindrical shape, i.e. the body 46 is tubular. It will be readily understood that the body 46 could alternatively have a completely different shape. It has to be noted that the various examples provided herein are not limitative and serve an illustrative purpose only.

Method

In accordance with another aspect, there is provided a method for analysing a soil located in an underground area. The method includes a step of inserting a probe head 24 in the underground area to contact the soil. As explained above, the probe head 24 includes a transparent wall 30 defining a hollow chamber 31 within the probe head 24 and the transparent wall 30 has a top extremity 33 and a bottom extremity 35. The top extremity 33 and the bottom extremity 35 define an optical path 37 therebetween.

After the step of inserting the probe head 24 in the underground area to contact the soil, the method includes a step of projecting an illuminating beam towards the soil and through the transparent wall 30 to irradiate the soil, thereby producing a resulting light emanating from the soil and returning towards the probe head 24. In some embodiments, projecting the illuminating beam towards the soil and through the transparent wall 30 to irradiate the soil includes irradiating the soil through 360 degrees around the probe head 24.

Once the resulting light has returned towards the probe head 24, the method includes a step of guiding, in the transparent wall 30, a portion of the resulting light by total internal reflection along the optical path 37.

The method also includes guiding, with an optical element 29, the portion of the resulting light guided in the transparent wall 30 from the transparent wall 30 to the detector 26. It has to be noted that the optical element 29 is generally provided near or at the top extremity 33 of the transparent wall 30, and as such, only the resulting light guided from the bottom extremity 35 (or elsewhere) and towards the top extremity 33 is affected by the optical element 29, meaning that it is typically the portion of the light guided by the transparent wall 30 that reaches the top extremity 33 of the transparent wall 35 that is guided towards the detector 26.

After the portion of the resulting light in the transparent wall 30 has been guided, a step of detecting the portion of the resulting light guided in the transparent wall 30 is carried out. After the portions of the portion of the resulting light guided in the transparent wall 30 is detected by the detector 26, the detector 26 outputs an output signal representative of the at least one characteristic of the soil. As it has been previously mentioned, the characteristics of the soil include, but are not limited to level of nutrients, level of available nutrients, ionic concentration of the soil solution, temperature, moisture, pH, and level of organic matter.

In some embodiments, the method also includes a step of processing the output signal representative of said at least one characteristic of the soil. The step of processing the output signal representative of the characteristic(s) of the soil can include, for example and without being limitative, receiving the output signal representative of the characteristic(s) of the soil and determining a spectral content of the portion of the resulting light guided in the transparent wall 30.

The method can be adapted to measure at least one of the electroconductivity and the pH of the soil with a sensing tip 48 mounted at an extremity of the probe head 24.

The optical probe 20 can be wirelessly operated, such that at least one of the light source 22 and the detector 26 is controlled at distance with a control unit or similar devices.

It has to be noted that the optical probe 20 can be inserted in the underground area using different device, apparatus, techniques and method. In a nonlimitative example, the method includes drilling a hole in the underground area to receive the probe head 24 therein. In another nonlimitive example, the method is adapted such that inserting the probe head 24 in the underground area to contact the soil includes pushing the probe head 24 towards the underground area. In this example, the method is optionally provided with a step of rotating the probe head 24 as the probe head 24 is pushed towards the underground area. When combined together, the steps of pushing and rotating the probe head 24 are similar to screwing the probe head 24 into the ground. In some embodiments, inserting the probe head 24 in the underground area to contact the soil includes inserting the probe head in a pre-made hole. The hole could be pre-drilled. The insertion of the probe head 24 can be made, for example and without being limitative, at a depth ranging from about 0 cm to about 80 cm.

While the method has been insofar described as having a single measurement step, it will have been readily understood that several measurement points are typically characterized in a field. For example, the method provided herein allows mapping the field at different geographical locations in order to obtain the characteristics of the soil at these different geographical locations or different depths (e.g., 15 cm and 30 cm). In these instances, the method includes obtaining one or more subsequent output signals representative of at least one characteristic of the soil. Each subsequent output signal is generally measured at a different location of the field one from another. Performing this step allows mapping the variations in different characteristics that might be present in the field, as it is often the case.

As such, the methods provided herein not only allow measuring properties of the soil in situ, but it can also be adapted to provide a map of the properties of the soil at various geographical points and depths of the field, thereby providing a global portrait of the field under investigation. This can be useful to provide some insights and analytics on the variable properties of the field, and thus can be used, for example and without being limitative, to identify trends in the dynamic of the field.

In accordance with one implementation, there is also provided a method for analysing a soil located in an underground area using an illuminating beam. Broadly described, the method according to this implementation includes inserting an optical probe including a light collector in the underground area to contact the soil; projecting the illuminating beam towards the soil through the light collector; collecting a resulting light reflected by the soil with the light collector; detecting the resulting light reflected by the soil; and outputting a signal representative of the soil condition. In some embodiments, the hole into which is inserted the optical probe can be made with a drilling device, such as for example and without being limitative an auger. In some embodiments, the hole can be made by inserting and pushing the optical probe into the ground. In some embodiments, the optical probe can be moved from one location to another to take measurements at different location of a field.

Several alternative embodiments and examples have been described and illustrated herein. The embodiments described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. The present examples and embodiments, therefore, are to be considered in all respects as illustrative and not restrictive. Accordingly, while specific embodiments have been illustrated and described, numerous modifications come to mind without significantly departing from the scope defined in the appended claims.

The invention claimed is:

1. An optical probe for analyzing a soil located in an underground area, the optical probe comprising:
    a probe head insertable into the underground area to contact the soil, the probe head comprising a transparent wall defining a hollow chamber within the probe head, the transparent wall having a top extremity and a bottom extremity defining an optical path therebetween, wherein the optical path is defined in a direction parallel to a distance between the top extremity and the bottom extremity;
    a light source mounted in the hollow chamber, the light source being configured to generate an illumination beam towards the soil, the illumination beam passing through the transparent wall to irradiate the soil, thereby producing a resulting light emanating from the soil, a portion of the resulting light returning towards the probe head and being guided in the transparent wall by total internal reflection along the optical path, wherein the portion of the resulting light being guided in the transparent wall propagates along the direction parallel to the distance between the top extremity and the bottom extremity;
    a detector configured to receive the portion of the resulting light guided in the transparent wall and outputting an output signal representative of at least one characteristic of the soil; and
    an optical element mounted in the hollow chamber, near or at the top extremity of the transparent wall, the optical element guiding the portion of the resulting light guided in the transparent wall from the transparent wall to the detector.

2. The optical probe of claim 1, wherein the light source comprises a light-emitting diode configured to emit the illumination beam, the illumination beam having a spectral profile comprising a waveband ranging from about 350 nm to about 900 nm or a visible waveband ranging from about 400 nm to about 750 nm.

3. The optical probe of claim 2, further comprising a first radial lens optically coupled to the light-emitting diode for generating a collimated illuminating beam.

4. The optical probe of claim 3, wherein the first radial lens is positioned at or near the bottom extremity, in the hollow chamber.

5. The optical probe of claim 1, wherein the light source comprises a stack of light-emitting diodes, the stack of light-emitting diodes comprising at least one of:
    a white broad band light-emitting diode;
    an infrared broad band light-emitting diode;
    a blue-light emitting diode; or
    an ultra-violet light-emitting diode.

6. The optical probe of claim 1, wherein the light source comprises a stack of light-emitting diodes, the stack of light-emitting diodes comprising at least one of:
    an ultra-violet light-emitting diode emitting an ultra-violet sub-beam having a spectral profile comprising a waveband centered around 385 nm;
    a blue light-emitting diode mounted on the ultra-violet light emitting diode and emitting a blue sub-beam having a spectral profile comprising a waveband centered around 488 nm;
    an infrared broad band light-emitting diode mounted on the blue-light emitting diode and emitting an infrared sub-beam having a spectral profile comprising a waveband ranging from about 650 nm to about 900 nm; and
a white broad band light-emitting diode mounted on the infrared broad band light-emitting diode and emitting a white sub-beam having a spectral profile comprising a waveband ranging from about 420 nm to about 700 nm.

7. The optical probe of claim 5, wherein each light-emitting diode from the stack of light-emitting diodes is optically coupled with a respective radial lens.

8. The optical probe of claim 1, wherein the portion of the resulting light guided by the transparent wall comprises light scattered by the soil and/or light reflected by the soil.

9. The optical probe of claim 1, wherein the transparent wall is tubular and the light source is configured to irradiate the soil through 360 degrees around the probe head, the probe head having an outer surface area ranging from about 400 mm$^2$ to about 4000 mm$^2$.

10. The optical probe of claim 1, wherein the transparent wall is made from a material impermeable to a soil solution present in the soil, the material impermeable to the soil solution being selected from the group consisting of: clear fused quartz, sapphire, and a transparent plastic.

11. The optical probe of claim 1, wherein the optical element comprises an optical diffuser positioned near or at the top extremity, in the hollow chamber, the optical diffuser being optically coupled with the transparent wall for scattering the portion of the resulting light guided in the transparent wall inside the probe head.

12. The optical probe of claim 1, wherein the detector comprises a spectrometer.

13. The optical probe of claim 1, wherein the optical probe further includes a processor, the processor being configured to:
receive the output signal representative of the at least one characteristic of the soil; and
determine a spectral content of the portion of the resulting light guided by the transparent wall.

14. The optical probe of claim 1, wherein the at least one characteristic of the soil is selected from the group consisting of: level of nutrients, level of available nutrients, ionic concentration of the soil solution, temperature, moisture, pH, level of organic matter, and soil texture.

15. The optical probe of claim 1, further comprising a sensing tip mounted at an extremity of the probe head, the sensing tip being configured to measure at least one of an electroconductivity and a pH of the soil.

16. The optical probe of claim 1, wherein the transparent wall comprises an inner surface and an outer surface, the resulting light returning towards the probe head and being guided in the transparent wall by total internal reflection travelling from the bottom extremity towards the top extremity, between the inner surface and the outer surface of the transparent wall.

17. A method for analyzing a soil located in an underground area, the method comprising:
inserting a probe head in the underground area to contact the soil, the probe head comprising a transparent wall defining a hollow chamber within the probe head, the transparent wall having a top extremity and a bottom extremity defining an optical path therebetween, wherein the optical path is defined in a direction parallel to a distance between the top extremity and the bottom extremity;
projecting an illuminating beam towards the soil and through the transparent wall to irradiate the soil, thereby producing a resulting light emanating from the soil and returning towards the probe head;
guiding, in the transparent wall, a portion of the resulting light by total internal reflection along the optical path, wherein the portion of the resulting light being guided in the transparent wall propagates along the direction parallel to the distance between the top extremity and the bottom extremity;
guiding, with an optical element, the portion of the resulting light guided in the transparent wall with an optical element from the transparent wall to a detector;
detecting the portion of the resulting light guided in the transparent wall; and
outputting an output signal representative of at least one characteristic of the soil.

18. The method of claim 17, wherein the at least one characteristic of the soil is selected from the group consisting of: level of nutrients, level of available nutrients, ionic concentration of the soil solution, temperature, moisture, pH, level of organic matter, and soil texture.

19. The method of claim 17, wherein the inserting the probe head in the underground area to contact the soil comprises inserting the probe head at a depth ranging from about 0 cm to about 80 cm.

20. The method of claim 17, further comprising obtaining one or more subsequent output signals representative of at least one characteristic of the soil, each subsequent output signal being measured at a different location of a field or at a different depth of the field.

21. The method of claim 17, wherein the projecting the illuminating beam towards the soil and through the transparent wall to irradiate the soil comprises irradiating the soil through 360 degrees around the probe head.

* * * * *